US011357972B2

(12) United States Patent
Po et al.

(10) Patent No.: US 11,357,972 B2
(45) Date of Patent: Jun. 14, 2022

(54) SYSTEM AND METHOD FOR TREATING AUTONOMIC NERVOUS SYSTEM DYSFUNCTIONS

(71) Applicant: The Board of Regents of the University of Oklahoma, Norman, OK (US)

(72) Inventors: Sunny Po, Edmond, OK (US); Benjamin Scherlag, Oklahoma City, OK (US); Stavros Stavrakis, Norman, OK (US); Paul Garabelli, Norman, OK (US); David Albert, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/955,238

(22) PCT Filed: Dec. 14, 2018

(86) PCT No.: PCT/US2018/065700
§ 371 (c)(1),
(2) Date: Jun. 18, 2020

(87) PCT Pub. No.: WO2019/125943
PCT Pub. Date: Jun. 27, 2019

(65) Prior Publication Data
US 2020/0324105 A1 Oct. 15, 2020

Related U.S. Application Data

(60) Provisional application No. 62/609,572, filed on Dec. 22, 2017.

(51) Int. Cl.
*A61N 1/04* (2006.01)
*A61N 1/08* (2006.01)
(Continued)

(52) U.S. Cl.
CPC ............. *A61N 1/0456* (2013.01); *A61N 1/08* (2013.01); *A61N 1/3625* (2013.01); *A61N 1/36031* (2017.08); *A61N 1/36592* (2013.01)

(58) Field of Classification Search
CPC .... A61N 1/0456; A61N 1/08; A61N 1/36031; A61N 1/3625; A61N 1/36592;
(Continued)

(56) References Cited

U.S. PATENT DOCUMENTS 6,341,236 B1 1/2002 Osorio et al.
8,005,545 B2 8/2011 Ben-David et al.
(Continued)

FOREIGN PATENT DOCUMENTS

WO 2017/173331 A1 10/2017
WO 2017190049 A1 11/2017

OTHER PUBLICATIONS

PCT International Search Report and Written Opinion for PCT Application No. PCT/US2018/065700 dated Feb. 22, 2019 (12 pages).

*Primary Examiner* — Carl H Layno
*Assistant Examiner* — Anh-Khoa N Dinh
(74) *Attorney, Agent, or Firm* — Eversheds Sutherland (US) LLP

(57) ABSTRACT

Methods and systems for alleviating disorders and complications associated with autonomic nervous system dysfunction. The approach generally includes measuring heart rate signals from a subject to measure heart rate variability and determine a heart rate variability threshold, determining that the subject is experiencing autonomic nervous system dysfunction, and alerting the subject to stimulate the auricular branch of the vagus nerve with an ear device.

18 Claims, 3 Drawing Sheets

(51) Int. Cl.
*A61N 1/36* (2006.01)
*A61N 1/362* (2006.01)
*A61N 1/365* (2006.01)

(58) Field of Classification Search
CPC ............ A61N 1/36036; A61N 1/3621; A61B 5/0022; A61B 5/02416; A61B 5/02438; A61B 5/4836; A61B 5/746; G16H 40/67
See application file for complete search history.

(56) References Cited

U.S. PATENT DOCUMENTS

| | | | |
|---|---|---|---|
| 2010/0274308 A1* | 10/2010 | Scott | A61N 1/36135 607/9 |
| 2013/0131746 A1* | 5/2013 | Simon | A61N 1/36034 607/9 |
| 2013/0158622 A1* | 6/2013 | Libbus | A61N 1/36114 607/27 |
| 2013/0245486 A1 | 9/2013 | Simon et al. | |
| 2014/0025132 A1* | 1/2014 | Libbus | A61N 1/365 607/17 |
| 2015/0360030 A1 | 12/2015 | Cartledge et al. | |
| 2016/0279021 A1* | 9/2016 | Hyde | A61H 23/02 |
| 2017/0043160 A1 | 2/2017 | Goodall et al. | |

\* cited by examiner

SYSTEM AND METHOD FOR TREATING AUTONOMIC NERVOUS SYSTEM DYSFUNCTIONS

CROSS REFERENCE TO RELATED APPLICATIONS

The present patent application claims the priority benefit of PCT/US2018/065700 filed on Dec. 14, 2018, and of provisional patent application U.S. Ser. No. 62/609,572, filed on Dec. 22, 2017, under 35 U.S.C. Sec. 119(e), the entire contents of which are incorporated herein by reference.

BACKGROUND

Hypertension (high blood pressure) and atrial fibrillation (irregular and rapid heart rhythm) are leading causes of cardiovascular mortality and stroke. Both diseases are known to be heavily influenced by enhanced activity of the autonomic nervous system.

Pharmacological therapy for hypertension is often complicated by sporadic increases of blood pressure as a result of higher sympathetic tone caused by emotional or physical stress. The standard medical practice is to increase the standing dose of the antihypertensive medicine. Frequently, higher doses of medications to treat sporadic increases of blood pressure leads to prolonged hypotension and increased risks of fall, particularly in elderly patients. The conventional "pill in pocket" approach has not been widely adopted due to the sustained pharmacological effects of the rescue pill which often leads to hypotension. A therapy that can treat sporadic hypertension without causing hypotension is in great demand.

Atrial fibrillation is known to be initiated by high autonomic activities. After initiation, atrial fibrillation often perpetuates itself and starts a vicious cycle of "atrial fibrillation begets atrial fibrillation." Sustained atrial fibrillation leads to the formation of blood clot in the heart, a leading cause of stroke. A therapy that can terminate atrial fibrillation before or shortly after its initiation may eliminate the need for long-term anticoagulation or ant-arrhythmic therapies, both of which are expensive and have significant adverse effects.

BRIEF DESCRIPTION OF THE DRAWINGS

Reference is now made to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments. The figures are not necessarily to scale and certain features and certain views of the figures may be shown as exaggerated in scale or in schematic in the interest of clarity and conciseness.

DETAILED DESCRIPTION

Figure 1:
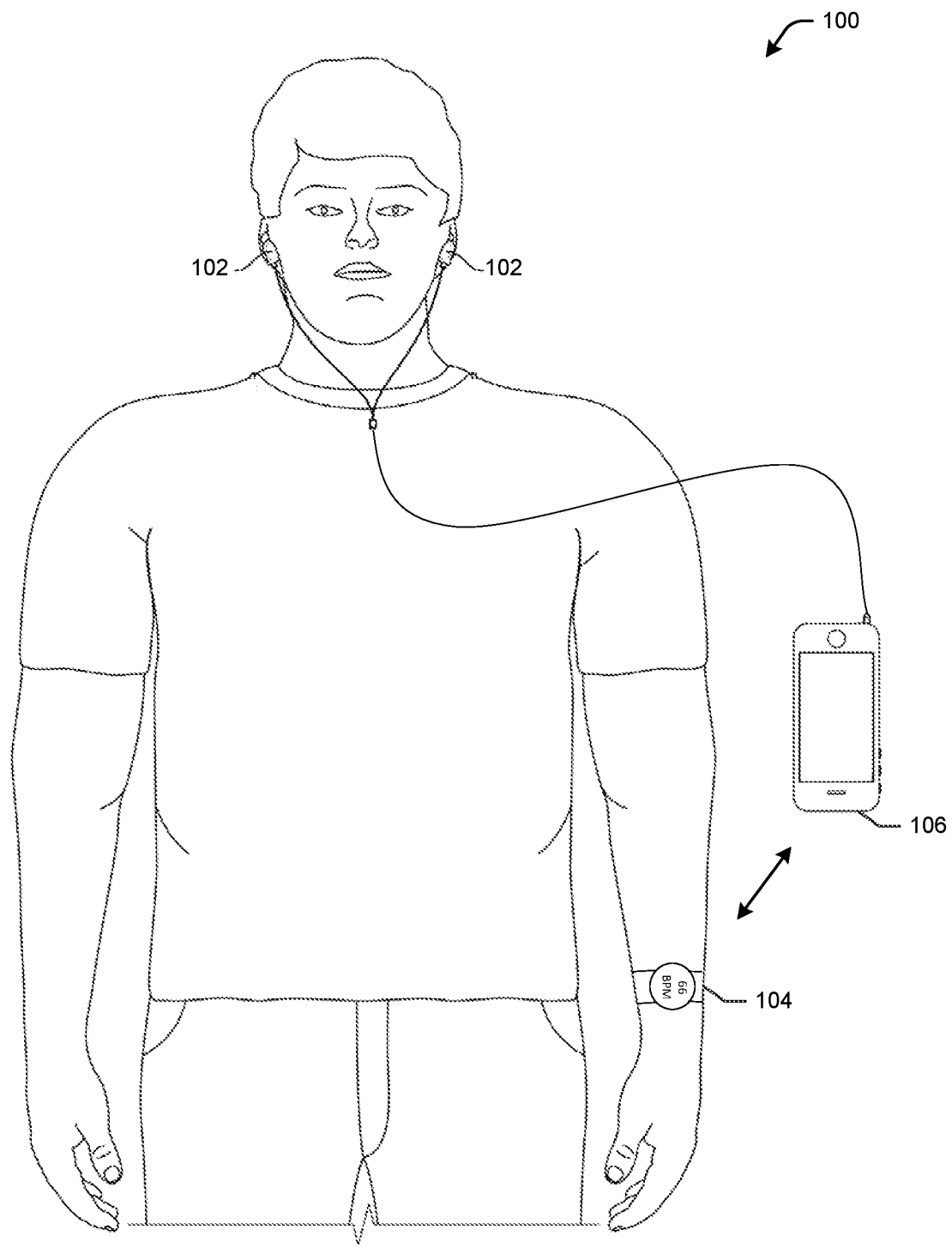
FIG. 1 shows an illustration of a system for managing autonomic nervous system dysfunction in accordance with one or more exemplary embodiments of the disclosure.

Systems and methods for stimulating the auricular branch of the vagus (tragus) nerve have been developed for treating a subject (e.g., a person) suffering from disorders and complications associated with autonomic nervous system (ANS) dysfunction. In certain embodiments, the systems include a small, unobtrusive device that the subject wears in or about his or her ear, like an ear-bud or ear-clip, and optionally another wearable device such as a wrist band. The ear device and wearable device are commonly connected to an ANS management device, which may be a smartphone or other remote device. In the systems, the ear device or wearable device includes one or more sensors, such as a sensor for detecting heart rate, and the ANS management device is configured to determine from information provided by the sensors when the subject experiences a disorder or complication associated with ANS dysfunction. In certain embodiments, for example, the systems monitor a subject's heart rate for detecting changes (e.g., decreases) in heart rate variability (HRV), and when the HRV is higher or lower than a predetermined threshold (HRV threshold number), determine that the subject is experiencing, or about to experience, atrial fibrillation, which is associated with abnormal ANS activity. The systems promptly respond to the disorder or complication by automatically starting, or alerting the subject (or a person able to act on behalf of the subject) to start transcutaneous stimulation of the vagus nerve using an electrode in the ear device, so as to ameliorate the ANS dysfunction and associated disorder or complication. In certain embodiments, the subject is a person who has been previously diagnosed with an ANS dysfunction such as paroxysmal atrial fibrillation.

Before describing various embodiments of the present disclosure in more detail by way of exemplary description, examples, and results, it is to be understood that the present disclosure is not limited in application to the details of systems, apparatus, and methods as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" or "approximately" is used to indicate that a value includes the inherent variation of error. Further, in this detailed description, each numerical value (e.g., time or frequency) should be read once as modified by the term "about" (unless already expressly so modified), and then read again as not so modified unless otherwise indicated in context. As noted, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. The use of the term "about" may mean a range including ±1%, or ±5%, or ±10%, or ±15%, or ±25% of the subsequent number unless otherwise stated.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The terms "subject" and "patient" are used interchangeably herein and will be understood to refer an animal to which the systems and methods of the present disclosure are applied and used, such as a vertebrate or more particularly to a warm blooded animal, such as a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments, such as for treating an ANS dysfunction. The term "treating" refers to administering the system or method to a subject for such therapeutic purposes, and may result in an amelioration of the condition or disease.

The term "effective amount" refers to an amount of a treatment, for example electrical stimulation of the auricular branch of the vagus nerve, which is sufficient to exhibit a detectable therapeutic effect, without excessive adverse side effects (such as toxicity, irritation, excessive heart rate) commensurate with a reasonable benefit/risk ratio when used in the manner of the present disclosure. The effective amount for a patient will depend upon the type of patient, the patient's size and health, the nature and severity of the ANS dysfunction to be treated, the method of administration, the duration of treatment, the nature of concurrent therapy (if any), the specific formulations employed, and the like. Thus, it is not possible to specify an exact effective amount in advance. However, the effective amount for a given situation can be determined by a person of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Returning now to the description of the various embodiments of the systems and methods of the present disclosure, in at least one embodiment, a subject (e.g., a person) wears an ear device throughout the day. The ear device measures physiological signals associated with heart rate and sends the physiological data to an ANS management device. The ANS management device processes the physiological signals and, in the event the ANS management device determines that the person's HRV has dropped below a threshold number indicative of a disorder or complication associated with ANS dysfunction, starts or signals to the person to start transcutaneous stimulation of the vagus nerve using the ear device. The low-level vagus nerve stimulation restores balance to ANS activity, particularly sympathetic and vagal balance.

In another non-limiting embodiment of the systems and methods of the present disclosure, a person (the subject) wears a wearable device such as a wrist band throughout the day. The wearable device measures physiological signals associated with heart rate and sends the physiological data to an ANS management device. The ANS management device processes the physiological signals and, in the event the ANS management device determines that the person's HRV has dropped below a threshold number indicative of a disorder or complication associated with ANS dysfunction, starts or signals to the person to start transcutaneous stimulation of the vagus nerve using the ear device. The low-level vagus nerve stimulation restores balance to an ANS activity, particularly sympathetic and vagal balance.

In certain embodiments, the systems and methods combine non-invasive heart rhythm monitoring with non-invasive nerve stimulation to alleviate hyperactivity of the ANS. In certain embodiments, the systems and methods provide neuromodulatory therapy which suppresses the activity of the ANS, particularly the sympathetic activity, without inducing any discomfort to a person or slowing their heart rate. The closed-loop autonomic neuromodulation is a safe and effective modality for treating ANS dysfunction and associated disorders or complications, such as atrial fibrillation and hypertension. The systems and methods of the present disclosure may vitiate the need for long-term pharmacological therapy for conditions that are sporadic in nature, thereby reducing medical costs and drug-induced adverse effects.

Turning now to the figures, FIG. 1 schematically shows a system 100 for managing ANS dysfunction in accordance with one or more exemplary embodiments of the disclosure. The system 100 may include one or more ear devices 102, one or more wearable devices 104, and/or one or more ANS management devices 106. The system 100 may be configured such that ear device(s) 102, wearable device(s) 104, and ANS management device(s) 106 are in communication with one another, thereby allowing data communication between the various devices. The devices may communicate with each other by any conventional means known in the art, such as through a wire (e.g. copper wire) or wireless communication 108 such as Bluetooth, Wi-Fi, and the like.

The ear device(s) 102 may be custom-fit earpiece(s) that match the contours of a person's ear and ear canal, headphones, earbud(s), ear-clip(s), hearing aid(s), or similar devices. Typical materials for producing the ear device(s) 102, and particularly a shell of the ear device(s) 102, include but not are limited to plastic materials and silicones. The ear device(s) 102 may be fully or partially disposable on or in a person's ears. When partially disposed in the ear, part of the ear device(s) 102 reside outside the ears such as is typical with behind-the-ear hearing aids or headphones. The ear device(s) 102 may attach to the external ear, for example at the tragus. The ear device(s) 102 may be configured such that a neural stimulator (discussed below) in the ear device(s) contacts the tragus and/or is capable of stimulating the auricular branch of the vagus nerve that supplies sensory innervation to the tragus. The ear device(s) 102 may be configured to perform some or all of the following functions: capture physiological signals, process physiological signals, communicate with other devices (e.g. send physiological data to other devices, receive instructions for nerve stimulation from other devices), and stimulate the vagus nerve.

The wearable device(s) 104 may be configured to capture physiological signals, be worn on or about a person at a location other than the ears, and process physiological data. The wearable device(s) 104 may be a health monitoring device such as a smartwatch, wristband device, a chest strap, smart clothing, and the like. The wearable device(s) 104 may be configured to perform some or all of the following functions: capture physiological signals, process physiological signals, and communicate with other devices (e.g. receive physiological data from other devices, send captured physiological data to other devices, send instructions for nerve stimulation to other devices).

The ANS management device(s) 106 may include any suitable computing device capable of receiving and processing physiological data including a mobile device (e.g. a smartphone or tablet), a laptop, a personal computer, a desktop computer, and the like. The ANS management device(s) 106 may generally facilitate processing of physiological information from a person and determining whether to provide vagus nerve stimulation when a disorder or complication associated with autonomic nervous system dysfunction is detected. The ANS management device(s) 106 may be configured to perform some or all of the following functions: process physiological signals and communicate with other devices (e.g. receive physiological data from other devices, send instructions for nerve stimulation to other devices).

The systems and methods may accomplish ANS dysfunction management with various combinations of devices. In certain embodiments, the systems and methods include one or more ear devices 102, one or more wearable devices 104, and one or more ANS management devices 106. In embodiments, the systems and methods include one or more ear devices 102 and one or more ANS management devices 106. In embodiments, the systems and methods include one or more ear devices 102 and one or more wearable devices 104.

In certain embodiments, the system 100 is configured to detect physiological changes associated with ANS dysfunction. For example, the system 100 is configured to perform photoplethysmography, which measures changes in blood flow by shining a light on the skin and measuring how it scatters off blood vessels. In these embodiments, a neuromodulation system device 200 (e.g. an ear device or a wearable device), discussed below, may include a reflective pulse oximeter (which comprises an optical emitter and a photodetector) and an accelerometer. The optical emitter may be arranged to shine an infrared light on a person's skin and the photodetector may be arranged to pick up the light that scatters off nearby blood vessels. The accelerometer, meanwhile, may measure a person's movement. A digital signal processor such as shown below (which can be housed in the same or a different neuromodulation system device 200) may analyze the data, removing noise like skin movement or sunlight, and may extract information like heart rate. The system 100 may determine whether a person is experiencing ANS dysfunction from the heart rate information, and stimulate the person's vagus nerve to restore balance to the person's ANS activity.

Figure 2:
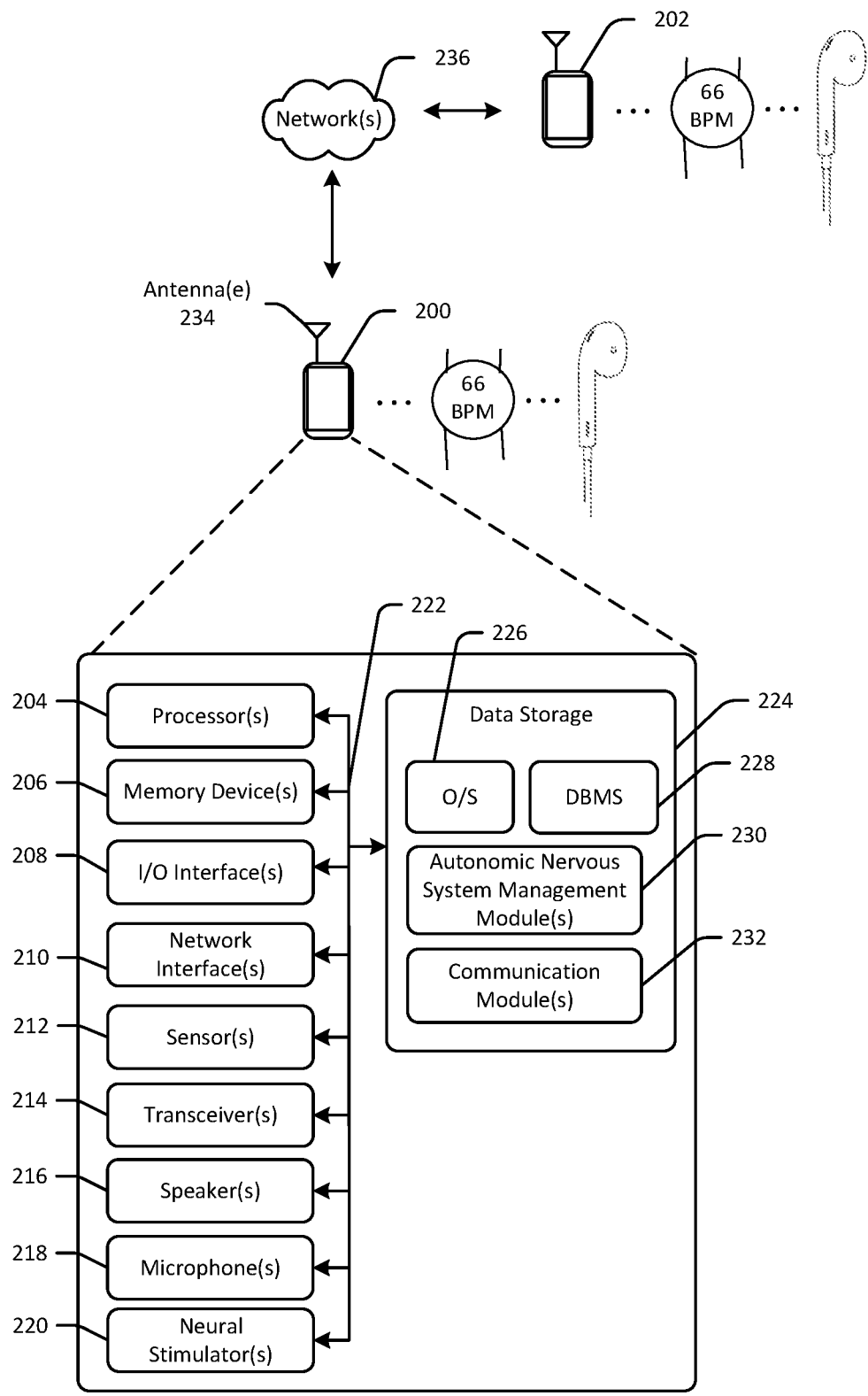
FIG. 2 is a schematic block diagram of an illustrative neuromodulation system device in accordance with one or more exemplary embodiments of the disclosure.

FIG. 2 is a schematic block diagram of a neuromodulation system device 200 in accordance with one or more exemplary embodiments of the disclosure. The neuromodulation system device 200 may correspond to an illustrative configuration for an ear device 102, a wearable device 104, and an ANS management device 106 of FIG. 1. The neuromodulation system device 200 may include some or all of the components shown in FIG. 2. The components included in a neuromodulation system device 200 may depend in part on whether the device is an ear device 102, a wearable device 104, or an ANS management device 106, and the desired functionality of the ear device 102, wearable device 104, or ANS management device 106.

The neuromodulation system device 200 may be configured to communicate via one or more networks 236 with one or more other neuromodulation system devices 202 (e.g. ear devices 102, wearable devices 104, ANS management devices 106), and the like. Network(s) 236 may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In one non-limiting embodiment as shown in FIG. 2, the neuromodulation system device 200 may optionally include one or more processors (processor(s)) 204, one or more memory devices 206 (generically referred to herein as memory 206), one or more input/output (I/O) interface(s) 208, one or more network interface(s) 210, one or more sensor(s) 212, one or more transceivers 214, one or more speakers 216, one or more microphones 218, one or more neural stimulators 220, and data storage 224. The neuromodulation system device 200 may further include one or more buses 222 that functionally couple the one or more various components of the neuromodulation system device 200. The neuromodulation system device 200 may further include one or more antenna(e) 234 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) 222 may include at least one of a system bus, a memory bus, an address bus, or a message bus, and may permit exchange of information (e.g., data (including computer-executable code), signaling, etc.) between various components of the neuromodulation system device 200. The bus(es) 222 may include, without limitation, a memory bus or a memory controller, a peripheral bus, an accelerated graphics port, and so forth. The bus(es) 222 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 206 of the neuromodulation system device 200 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 206 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 206 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 224 may include removable storage and/or non-removable storage including, but not limited to, magnetic storage, optical disk storage, and/or tape storage. The data storage 224 may provide non-volatile storage of computer-executable instructions and other data. The memory 206 and the data storage 224, removable and/or non-removable, are examples of computer-readable storage media (CRSM) as that term is used herein.

The data storage 224 may store computer-executable code, instructions, or the like that may be loadable into the memory 206 and executable by the processor(s) 204 to cause the processor(s) 204 to perform or initiate various operations. The data storage 224 may additionally store data that may be copied to memory 206 for use by the processor(s) 204 during the execution of the computer-executable instructions. Moreover, output data generated as a result of execution of the computer-executable instructions by the processor(s) 204 may be stored initially in memory 206 and may ultimately be copied to data storage 224 for non-volatile storage.

More specifically, the data storage 224 may store one or more operating systems (O/S) 226; one or more database management systems (DBMS) 228; and one or more program module(s), applications, engines, computer-executable code, scripts, or the like such as, for example, one or more ANS management module(s) 230. Any of the components depicted as being stored in data storage 224 may include any combination of software, firmware, and/or hardware. The software and/or firmware may include computer-executable code, instructions, or the like that may be loaded into the memory 206 for execution by one or more of the processor(s) 204. Any of the components depicted as being stored in data storage 224 may support functionality described in reference to correspondingly named components throughout this disclosure.

The data storage 224 may further store various types of data utilized by components of the neuromodulation system device 200. Any data stored in the data storage 224 may be loaded into the memory 206 for use by the processor(s) 204 in executing computer-executable code. In addition, any data depicted as being stored in the data storage 224 may potentially be stored in one or more datastore(s) and may be accessed via the DBMS 228 and loaded in the memory 206 for use by the processor(s) 204 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. In FIG. 2, the datastore(s) may include, for example, heart rate information, HRV information, and other physiological information.

The processor(s) 204 may be configured to access the memory 206 and execute computer-executable instructions loaded therein. For example, the processor(s) 204 may be configured to execute computer-executable instructions of the various program module(s), applications, engines, or the like of the neuromodulation system device 200 to cause or facilitate various operations to be performed in accordance with one or more embodiments of the disclosure. The processor(s) 204 may include any suitable processing unit capable of accepting data as input, processing the input data in accordance with stored computer-executable instructions, and generating output data. The processor(s) 204 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 204 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 204 may be capable of supporting any of a variety of instruction sets.

Referring now to functionality supported by the program module(s) depicted in FIG. 2, the ANS management module(s) 230 may include computer-executable instructions, code, or the like that responsive to execution by one or more of the processor(s) 204 may perform functions including, but not limited to, processing and monitoring physiological data (e.g. heart rate, HRV), determining from physiological data in real-time or near real-time whether a person is experiencing autonomic nervous system dysfunction, stimulating or causing stimulation of the vagus nerve, sending or causing to send an alert to start stimulation of the vagus nerve, and the like. The ANS management module(s) 230 may be configured to digitize captured analog signals and analyze specific features or changes in captured signals at a discrete time or over a period of time to detect or predict the occurrence of a biological condition, state, or incident (e.g., ANS dysfunction). If the ANS management module(s) 230 detects a biological condition, state, or incident in a person, the module(s) may respond by stimulating, or instructing a person or another device to stimulate, a person's autonomic nervous system.

The communication module(s) 232 may include computer-executable instructions, code, or the like that responsive to execution by one or more of the processor(s) 204 may perform functions including, but not limited to, communicating with one or more other neuromodulation system devices 202 (e.g. ear devices 102, wearable devices 104, ANS management devices 106), for example, via wired or wireless communication, communicating with remote servers, communicating with remote datastores, sending or receiving information, communicating with cache memory data, and the like.

Referring now to other illustrative components depicted as being stored in the data storage 224, the O/S 226 may be loaded from the data storage 224 into the memory 206 and may provide an interface between other application software executing on the neuromodulation system device 200 and hardware resources of the neuromodulation system device 200. More specifically, the O/S 226 may include a set of computer-executable instructions for managing hardware resources of the neuromodulation system device 200 and for providing common services to other application programs (e.g., managing memory allocation among various application programs). In certain example embodiments, the O/S 226 may control execution of the program module(s). The O/S 226 may include any operating system now known or which may be developed in the future including, but not limited to, any server operating system, any mainframe operating system, or any other proprietary or non-proprietary operating system.

The DBMS 228 may be loaded into the memory 206 and may support functionality for accessing, retrieving, storing, and/or manipulating data stored in the memory 206 and/or data stored in the data storage 224. The DBMS 228 may use any of a variety of database models (e.g., relational model, object model, etc.) and may support any of a variety of query languages. The DBMS 228 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the neuromodulation system device 200 is a mobile device, the DBMS 228 may be any suitable light-weight DBMS optimized for performance on a mobile device.

Referring now to other illustrative components of the neuromodulation system device 200, the input/output (I/O) interface(s) 208 may facilitate the receipt of input information by the neuromodulation system device 200 from one or more I/O devices as well as the output of information from the neuromodulation system device 200 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the neuromodulation system device 200 or may be separate. The I/O devices may further include, for example, any number of peripheral devices such as data storage devices, and so forth.

The I/O interface(s) 208 may also include an interface for an external peripheral device connection such as universal serial bus (USB), FireWire, Thunderbolt, Ethernet port or other connection protocol that may connect to one or more networks. The I/O interface(s) 208 may also include a connection to one or more of the antenna(e) 234 to connect to one or more networks via a wireless local area network (WLAN) (such as Wi-Fi) radio, Bluetooth, ZigBee, and/or a wireless network radio, such as a radio capable of communication with a wireless communication network such as a Long Term Evolution (LTE) network, WiMAX network, 3G network, ZigBee network, etc.

The neuromodulation system device 200 may further include one or more network interface(s) 210 via which the neuromodulation system device 200 may communicate with any of a variety of other systems, platforms, networks, devices, and so forth. The network interface(s) 210 may enable communication, for example, with one or more wireless routers, one or more host servers, one or more web servers, one or more other neuromodulation system devices 202, and the like via one or more of networks.

The antenna(e) 234 may include any suitable type of antenna depending, for example, on the communications protocols used to transmit or receive signals via the antenna (e) 234. Non-limiting examples of suitable antennas may include directional antennas, non-directional antennas, dipole antennas, folded dipole antennas, patch antennas, multiple-input multiple-output (MIMO) antennas, or the like. The antenna(e) 234 may be communicatively coupled to one or more transceivers 214 or radio components to which or from which signals may be transmitted or received.

As previously described, the antenna(e) 234 may include a cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like.

The antenna(e) 234 may additionally, or alternatively, include a Wi-Fi antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11ad). In alternative example embodiments, the antenna(e) 234 may be configured to transmit or receive radio frequency signals within any suitable frequency range forming part of the unlicensed portion of the radio spectrum.

The transceiver(s) 214 may include any suitable radio component(s) for, in cooperation with the antenna(e) 234, transmitting or receiving radio frequency (RF) signals in the bandwidth and/or channels corresponding to the communications protocols utilized by the neuromodulation system device 200 to communicate with other devices. The transceiver(s) 214 may include hardware, software, and/or firmware for modulating, transmitting, or receiving, potentially in cooperation with any of antenna(e) 234, communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 214 may include any known receiver and baseband suitable for communicating via the communications protocols utilized by the neuromodulation system device 200. The transceiver(s) 214 may further include a low noise amplifier (LNA), additional signal amplifiers, an analog-to-digital (A/D) converter, one or more buffers, a digital baseband, or the like.

The sensor(s) 212 may include biosensors that capture and convert a biological or physiological response or measurement into an electrical signal. In embodiments which include more than one sensor 212, the sensor(s) 212 can be of the same type, of different types, or combinations thereof. The sensor(s) 212 may include, for example, reflective pulse oximeters, inertial sensors (e.g. accelerometers, gyroscopes), and the like.

Reflective pulse oximeters can optically measure heart rate in a person by measuring varying peripheral perfusion. Reflective pulse oximeters can be used to detect, for example, abnormalities in HRV that can be indicative of autonomic nervous system dysfunction. Inertial sensors can measure and reports a body's specific force and angular rate using a combination of accelerometers and gyroscopes. Inertial sensors can be used to remove motion artifacts from measured signals.

The speaker(s) 216 may be any device configured to generate audible sound. The optional microphone(s) 218 may be any device configured to receive analog sound input or voice data.

The neural stimulator(s) 220 may be any device or component configured to stimulate the vagus nerve. The neural stimulator(s) 220 may include one or more electrodes for transcutaneous electrical nerve stimulation. The electrodes may be polarizable electrodes or non-polarizable electrodes. Polarizable electrodes are electrodes transferring a potential capacitively, i.e., with little or without any transport of charges from the skin to the electrode. Non-polarizable electrodes are electrodes by which a transport of charges between the skin and the electrode is conducted with little or without loss of energy in the transition between skin and electrode. In such electrodes a transformation occurs in the transition from ion transport in the skin to electron transport in the electrode, whereby a current is running in the transition.

In certain embodiments, the electrodes are made of materials that confer durability to the electrodes when exposed to the conditions of the human ear. For polarizable electrodes such materials can include, but are not limited to, an alloy such as stainless steel or platinum-iridium, or a noble metal such as silver, titanium, platinum, or tungsten. Non-polarizable electrodes are typically made of silver-silver chloride (Ag/AgCl). However, any suitable material can be used for the polarizable or non-polarizable electrodes.

It should be appreciated that the program module(s), applications, computer-executable instructions, code, or the like depicted in FIG. 2 as being stored in the data storage 224 are merely illustrative and not exhaustive and that processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the neuromodulation system device 200, and/or hosted on other computing device(s) accessible via one or more networks, may be provided to support functionality provided by the program module(s), applications, or computer-executable code depicted in FIG. 2 and/or additional or alternate functionality. Further, functionality may be modularized differently such that processing described as being supported collectively by the collection of program module(s) depicted in FIG. 2 may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model such as, for example, a client-server model, a peer-to-peer model, and so forth. In addition, any of the functionality described as being supported by any of the program module(s) depicted in FIG. 2 may be implemented, at least partially, in hardware and/or firmware across any number of devices.

The neuromodulation system device 200 may include alternate and/or additional hardware, software, or firmware components beyond those described or depicted without departing from the scope of the disclosure. More particularly, software, firmware, or hardware components depicted as forming part of the neuromodulation system device 200 are merely illustrative; some components may not be present or additional components may be provided in various embodiments. While various illustrative program module(s) have been depicted and described as software module(s) stored in data storage 224, it will be appreciated by a person having ordinary skill in the art that functionality described as being supported by the program module(s) may be enabled by any combination of hardware, software, and/or firmware. Each of the above-mentioned module(s) may, in various embodiments, represent a logical partitioning of supported functionality. This logical partitioning is depicted for ease of explanation of the functionality and is not necessarily representative of the structure of software, hardware, and/or firmware for implementing the functionality. Accordingly, functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more exemplary embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, data processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Figure 3:
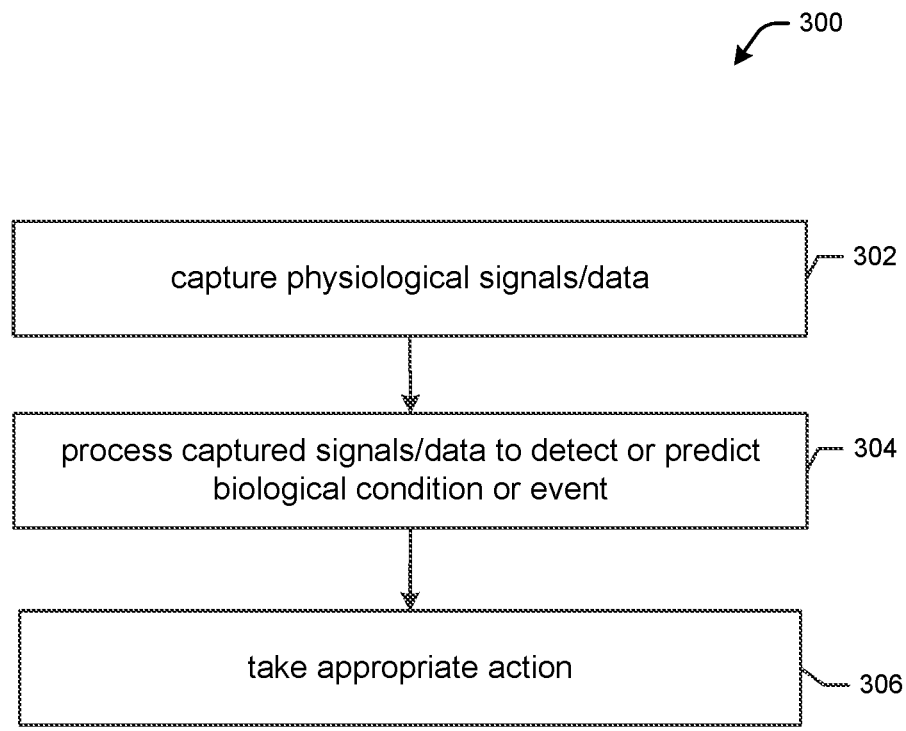
FIG. 3 shows a flowchart of a method for managing autonomic nervous system dysfunction in accordance with one or more exemplary embodiments of the disclosure.

FIG. 3 is a flowchart of a method 300 for managing ANS dysfunction in accordance with one or more example embodiments of the disclosure. The method 300 generally comprises monitoring physiological signals in a person, predicting or detecting the occurrence of a biological condition, state, or incident in a person from the physiological signals, and taking remedial action when the occurrence of a biological condition, state, or incident is predicted or detected. For example, various combinations of ear device(s), wearable device(s), and remote device(s) can form a system that monitors the heart rate and heart rate variability (HRV) in a person who may be afflicted with or at risk for an ANS dysfunction. The system can employ an algorithm that detects an occurrence of an ANS dysfunction, such as when a person's HRV drops below a threshold value indicative of elevated sympathetic tone associated with a disease or condition such as atrial fibrillation, hypertension, and the like. When the system determines that a person has an ANS dysfunction, the system starts, or alerts a person to start, low-level transcutaneous stimulation of the auricular branch of the vagus nerve via the ear device(s) or other appropriate device as disclosed herein.

In step 302, one or more neuromodulation system device(s) 200 capture (e.g. measure, gather, record) physiological signals. The neuromodulation system device(s) 200 that capture physiological signals may be ear devices(s), wearable device(s), or a combination thereof. Neuromodulation system device(s) 200 may capture a variety of physiological responses such as heart rate as well as contextual information such as acceleration.

In embodiments, the neuromodulation system device(s) 200 that capture physiological signals may passively capture physiological signals and/or contextual information for a period of time (e.g. for an hour, day, month, year, indefinitely). The passive capture of physiological signals and/or contextual information can be continuous (e.g. streaming) or discrete (e.g. once every five seconds, once per minute, once every five minutes, once per hour, once per day, etc.). The neuromodulation system device(s) 200 can begin or cease passively capturing information or change the frequency with which information is captured (e.g. increase or decrease information capture rate) when a physiological event occurs. For example, the system may detect or determine that ANS dysfunction is occurring, which can trigger the neuromodulation system device(s) to begin continuous monitoring of physiological signals.

The captured physiological signals and/or contextual information may be processed on the neuromodulation system device(s) which capture the data. The captured physiological signals and/or contextual information may be sent to other neuromodulation system device(s) for processing. The captured physiological signals and/or contextual information may be both processed on the neuromodulation system device(s) which capture the data as well as sent to other neuromodulation system device(s) for processing.

In step 304, captured information is processed. Processing can include amplification, filtering, converting, range matching, isolation, and other similar steps to prepare the captured information for analysis. Processing can include determining diagnostically relevant information from raw physiological data. For example, HRV information may be determined from captured heart rate information.

Processing can include predicting, determining, or detecting the occurrence of a biological condition, state, or incident in a person from the captured physiological signals. Processing can include determining whether a person's physiological measurements indicate the occurrence of an ANS dysfunction. Processing can include determining a change in HRV and determining that the change is associated with a disorder or condition associated with elevated sympathetic tone such as atrial fibrillation or high blood pressure. Processing can include determining whether a person's physiological measurements fall below, at, or above a threshold value indicative of an ANS dysfunction. Physiological measurements may indicate the occurrence of ANS dysfunction when they fall below, at, or above a threshold value indicative of an ANS dysfunction. The threshold value may be disease specific. That is, a threshold value indicative of atrial fibrillation may be different from a threshold value indicative of high blood pressure. In one embodiment, processing can include determining a change in HRV and determining whether the change falls below, at, or above a threshold value indicative of atrial fibrillation. In one embodiment, processing can include determining a change in HRV and determining whether the change falls below, at, or above a threshold value indicative of high blood pressure (hypertension).

Any neuromodulation system device(s) 200 may be used to process captured information, including ear devices(s), wearable device(s), remote device(s), and combinations thereof.

In step 306, an appropriate action is taken based on the results of step 304. If the occurrence of a biological condition, state, or incident is not predicted or detected, the system may continue monitoring physiological signals but take no action with respect to nerve stimulation. For example, if the system determines that a person's ANS activity is balanced and/or normal, the system may continue monitoring physiological signals but take no action with respect to nerve stimulation. Alternatively, if the occurrence of a biological condition, state, or incident is predicted or detected, the system may continue monitoring physiological signals and/or start, or alert a person to start, low-level transcutaneous stimulation of the auricular branch of the vagus nerve. For example, if the system determines that a person is experiencing an ANS dysfunction, the system may continue monitoring physiological signals and/or start, or alert a person to start, low-level transcutaneous stimulation of the auricular branch of the vagus nerve.

In certain embodiments, after the system determines that a person is experiencing an ANS dysfunction, the system automatically begins stimulating the vagus nerve through an ear device (or other device described herein). In embodiments, after the system determines that a person is experiencing autonomic nervous system dysfunction, the system alerts a person to start stimulating the vagus nerve through an ear device (or other device described herein). The alert may be, for example, an audible alert (e.g. alarm or sound), a visible alert (e.g. a screen notification or a text-based alert such as a text message), and/or a tactile alert (e.g. vibration). In response to an alert, a person may insert or attach an ear device (or other device described herein) if the person is not already wearing the ear device (or other device), and stimulation of the vagus nerve may begin.

In certain embodiments, stimulating the vagus nerve may include placing an electrode of an ear device on a person's tragus, and having the system or a person transcutaneously stimulate the vagus nerve. The vagus nerve may be stimulated for a period of time sufficient to ameliorate the ANS dysfunction. The period of time may be, for example, 5, 10, 20, 30, 45, 60 or more minutes. The vagus nerve may be stimulated at a stimulation strength below a discomfort threshold such that the person may not experience discomfort during stimulation. The discomfort threshold may be determined, for example, by gradually increasing stimulation strength until a person experiences mild discomfort, and then decreasing the stimulation strength by 1 mA below that threshold. In one embodiment, the ear device may be configured to stimulate the vagus nerve with a 100 μs pulse width and a 20 Hz pulse frequency, at an amplitude typically in the range of 10-50 mA.

In at least certain embodiments, HRV is defined as the variation in the time interval between heartbeats and is measured by the variation in the beat-to-beat interval. Beat-to-beat interval can be measured, in one non-limiting embodiment, by measuring the time interval between the major peaks ("RR interval") in adjacent "normal" QRS complexes ("NN intervals") in electrocardiogram waves over a particular duration of time, such as, but not limited to, durations of 1 to 5 minutes, for example, 1, 2, 3, 4, or 5 minutes. In another non-limiting embodiment, HRV can be determined by measuring a subject's pulse to determine the average time between heart beats. Statistics such as mean, standard deviation, or other forms of statistical variance can then be calculated from these measurements as measures of HRV for use in the systems and methods of the present disclosure. In a non-limiting embodiment, the HRV threshold for a particular person is determined by tracking the HRV of the person for a period of time (e.g., 1 hour to 6 months or longer, 1 hour to 24 hours, 1 day to 3 days, 1 day to 7 days, 1 day to 14 days, 1 day to 28 days, over 1 month to 6 months, or longer) until an episode of ANS dysfunction occurs (e.g., an episode of paroxysmal atrial fibrillation). The HRV threshold that is selected for that particular person is an HRV number in a a series of HRV numbers that occurred in a range of, for example, 10 seconds to 10 minutes to 15 minutes to 20 minutes to 30 minutes prior to the episode of ANS dysfunction (e.g., paroxysmal atrial fibrillation). Non-limiting examples of methods for measuring HRV are shown in U.S. Pat. Nos. 9,265,430 and 9,669,218, both of which are hereby explicitly incorporated herein by reference.

In one example embodiment, the method 300 for managing an ANS dysfunction can include capturing heart rate information through a reflective pulse oximeter disposed in an ear device or a wearable device, processing the captured heart rate information to determine whether there is a change in HRV that falls below, at, or above a threshold value indicative of atrial fibrillation, high blood pressure, or other relevant physiological condition, and starting or alerting a person to start stimulation of the auricular branch of the vagus nerve.

In step 302 of the example embodiment, an ear device or a wearable device passively captures throughout the day signals from a reflective pulse oximeter disposed on or in the ear device or wearable device.

In step 304, the raw signals from the reflective pulse oximeter, which are analog signals, are converted to digital form using an analog-to-digital converter as close as possible to the signal source to allow for an improved signal-to-noise ratio. The digitized signals are then transmitted to an ANS management device (e.g., smartphone) using a wireless connection (e.g., Bluetooth) or a wired connection. The digitized signals are filtered at the ANS management device to remove motion artifacts. The ANS management device then analyzes the signals to determine whether a change in a person's HRV falls below, at, or above a threshold value indicative of atrial fibrillation or high blood pressure.

In step 306 of the example embodiment, an appropriate action is taken based on the results of step 304. For example, if the system determines that a person's ANS activity is balanced and/or normal (e.g., no atrial fibrillation or high blood pressure), no action is taken. However, if the analysis determines that a person is experiencing, or is likely to experience, an ANS dysfunction (e.g., atrial fibrillation or high blood pressure), the ANS management device alerts/instructs the person to begin vagus nerve stimulation using the ear device and/or causes the ear device to stimulate the vagus nerve.

Therefore, in at least certain non-limiting embodiments, the present disclosure is directed to:

Clause 1. A system for managing an autonomic nervous system (ANS) dysfunction, comprising:
    an ear device configured to be worn on a subject's ear and and comprising a neural stimulator able to stimulate the subject's vagus nerve by transcutaneous stimulation;
    a sensor configured to detect heart rate signals; and
    an ANS management device in communication with the ear device, wherein the ANS management device comprises:
        a memory that stores computer-executable instructions, wherein the computer-executable instructions comprise instructions to determine whether the subject is experiencing an ANS dysfunction; and
    a processor configured to access the memory and execute the computer-executable instructions.

Clause 2. The system of clause 1, wherein the computer-executable instructions to determine whether the subject is experiencing the ANS dysfunction comprise instructions to measure a heart rate variability (HRV) in the subject, and determine when the HRV is lower than an HRV threshold number indicative of the ANS dysfunction.

Clause 3. The system of clause 2, wherein the HRV threshold number is determined by tracking the HRV of the subject for a period of time until an episode of ANS dysfunction occurs.

Clause 4. The system of clause 3, wherein the HRV threshold number is selected from a series of HRV numbers which occurred during a range of from about 10 seconds to about 20 minutes prior to the episode of ANS dysfunction.

Clause 5. The system of clause 2, wherein the computer-executable instructions comprise instructions to output an alert when the subject's HRV is less than the HRV threshold number.

Clause 6. The system of clause 5, wherein the alert is at least one alert selected from the group consisting of a visual alert, an audio alert, a text-based alert, and a tactile alert.

Clause 7. The system of any one of clauses 1 to 6, wherein the computer-executable instructions comprise instructions to output an alert to begin vagus nerve stimulation.

Clause 8. The system of any one of clauses 1 to 7, wherein the ear device is arranged to clip onto the subject's tragus.

Clause 9. The system of any one of clauses 1 to 8, wherein the sensor configured to detect heart rate is a component of the ear device.

Clause 10. The system of any one of clauses 1 to 9, further comprising a wearable device in communication with the ANS management device, wherein the sensor configured to detect heart rate is a component of the wearable device.

Clause 11. The system of clause 10, wherein the wearable device is selected from the group consisting of a smartwatch, a wristband device, and a chest strap.

Clause 12. A method for managing an autonomic nervous system (ANS) dysfunction in a subject, comprising:
providing a system comprising:
an ear device configured to be worn on the subject's ear and and comprising a neural stimulator able to stimulate the subject's vagus nerve by transcutaneous stimulation;
a sensor configured to detect heart rate signals in the subject; and
an ANS management device in communication with the ear device, wherein the ANS management device comprises:
a memory that stores computer-executable instructions, wherein the computer-executable instructions comprise instructions to determine whether the subject is experiencing an ANS dysfunction; and
a processor configured to access the memory and execute the computer-executable instructions;
measuring heart rate signals from the subject and determining a heart rate variability (HRV) from said heart rate signals;
comparing the HRV to a predetermined HRV threshold number; and
providing an alert to the subject when the HRV is lower than the HRV threshold number.

Clause 13. The method of clause 12, wherein the HRV threshold number is determined by tracking the HRV of the subject for a period of time until an episode of ANS dysfunction occurs.

Clause 14. The system of of clause 12 or 13, wherein the HRV threshold number is selected from a series of HRV numbers which occurred during a range of from about 10 seconds to about 20 minutes prior to the episode of ANS dysfunction.

Clause 15. The method of any one of clauses 12 to 14, wherein the neural stimulator is activated to stimulate the subject's vagus nerve by transcutaneous stimulation when the alert indicates that the HRV measurement is lower than the HRV threshold number.

Clause 16. The method of clause 15, wherein the subject's vagus nerve is stimulated for at least five minutes.

Clause 17. The method of clause 15 or 16, wherein the subject's vagus nerve is stimulated at a level below a discomfort threshold.

Clause 18. The method of any one of clauses 12 to 17, wherein the ANS dysfunction is selected from atrial fibrillation and hypertension.

Clause 19. The method of clause 18, wherein the atrial fibrillation is a paroxysmal atrial fibrillation.

Clause 20. The method of any one of clauses 12 to 19, wherein the alert is at least one alert selected from the group consisting of a visual alert, an audio alert, a text-based alert, and a tactile alert.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the systems and apparatus described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A system for managing an autonomic nervous system (ANS) dysfunction, comprising:
an ear device configured to be worn on a subject's ear and comprising a neural stimulator able to stimulate the subject's vagus nerve by transcutaneous stimulation;
a sensor configured to detect heart rate signals; and
an ANS management device in communication with the ear device, wherein the ANS management device comprises:
a memory that stores computer-executable instructions, wherein the computer-executable instructions comprise instructions to:
monitor the heart rate signals to determine whether the subject is experiencing an ANS dysfunction;
determine, based on the heart rate signals, the subject is experiencing the ANS dysfunction;

cause the sensor to increase a frequency at which the sensor detects the heart rate signals in response to an indication that the subject is experiencing the ANS dysfunction;

cause, based on the heart rate signal indicating the subject is experiencing the ANS dysfunction, stimulation of the subject's vagus nerve by the neural stimulator; and continue to monitor the heart rate signals to determine whether further stimulation of the subject's vagus nerve should be applied to ameliorate the ANS dysfunction; and a processor configured to access the memory and execute the computer-executable instructions.

2. The system of claim 1, wherein the computer-executable instructions to determine whether the subject is experiencing the ANS dysfunction comprise instructions to measure a heart rate variability (HRV) in the subject, and determine when the HRV is lower than an HRV threshold number indicative of the ANS dysfunction.

3. The system of claim 2, wherein the HRV threshold number is determined by tracking the HRV of the subject for a period of time until an episode of ANS dysfunction occurs.

4. The system of claim 3, wherein the HRV threshold number is selected from a series of HRV numbers which occurred during a range of from about 10 seconds to about 20 minutes prior to the episode of ANS dysfunction.

5. The system of claim 2, wherein the computer-executable instructions comprise instructions to output an alert when the subject's HRV is less than the HRV threshold number.

6. The system of claim 5, wherein the alert is at least one alert selected from the group consisting of a visual alert, an audio alert, a text-based alert, and a tactile alert.

7. The system of claim 1, wherein the ear device is arranged to clip onto the subject's tragus.

8. The system of claim 1, wherein the sensor configured to detect heart rate is a component of the ear device.

9. The system of claim 1, further comprising a wearable device in communication with the ANS management device, wherein the sensor configured to detect heart rate is a component of the wearable device.

10. The system of claim 9, wherein the wearable device is selected from the group consisting of a smartwatch, a wristband device, and a chest strap.

11. A method for managing an autonomic nervous system (ANS) dysfunction in a subject, comprising:
providing a system comprising:
an ear device configured to be worn on the subject's ear and comprising a neural stimulator able to stimulate the subject's vagus nerve by transcutaneous stimulation;
a sensor configured to detect heart rate signals in the subject; and
an ANS management device in communication with the ear device, wherein the ANS management device comprises:
a memory that stores computer-executable instructions, wherein the computer-executable instructions comprise instructions to determine whether the subject is experiencing an ANS dysfunction; and
a processor configured to access the memory and execute the computer-executable instructions;

measuring heart rate signals from the subject and determining a first heart rate variability (HRV) from said heart rate signals;

comparing the first HRV to a predetermined HRV threshold number;

when the first HRV is lower than the HRV threshold number, causing the neural stimulator to stimulate the subject's vagus nerve;

increasing a frequency at which the sensor detects the heart rate signals in response to an indication that the subject is experiencing the ANS dysfunction;

continuing to measure the heart rate signal from the subject to determine a second heart rate variability (HRV); and determining whether to cause further stimulation of the subject's vagus nerve based on the second HRV.

12. The method of claim 11, wherein the HRV threshold number is determined by tracking the first HRV of the subject for a period of time until an episode of ANS dysfunction occurs.

13. The system of claim 12, wherein the HRV threshold number is selected from a series of HRV numbers which occurred during a range of from about 10 seconds to about 20 minutes prior to the episode of ANS dysfunction.

14. The method of claim 11, wherein the neural stimulator is activated to stimulate the subject's vagus nerve by transcutaneous stimulation when an alert indicates that the first HRV measurement is lower than the HRV threshold number.

15. The method of claim 14, wherein the subject's vagus nerve is stimulated for at least five minutes.

16. The method of claim 14, wherein the subject's vagus nerve is stimulated at a level below a discomfort threshold.

17. The method of claim 11, wherein the ANS dysfunction is selected from atrial fibrillation and hypertension.

18. The method of claim 17, wherein the atrial fibrillation is a paroxysmal atrial fibrillation.

* * * * *